United States Patent [19]
Parker

[11] Patent Number: 6,155,966
[45] Date of Patent: Dec. 5, 2000

[54] APPARATUS AND METHOD FOR TONING TISSUE WITH A FOCUSED, COHERENT ELECTROMAGNETIC FIELD

[76] Inventor: Lloyd S. Parker, 10993 Bluffside Dr., Apt. 2304, Studio City, Calif. 91604

[21] Appl. No.: 09/193,472

[22] Filed: Nov. 17, 1998

[51] Int. Cl.[7] ........................................................ A61B 5/00
[52] U.S. Cl. ................................................................ 600/13
[58] Field of Search ........................................ 600/13, 14

[56] References Cited

U.S. PATENT DOCUMENTS

| | | | |
|---|---|---|---|
| 5,017,185 | 5/1991 | Baermann | 600/15 |
| 5,030,196 | 7/1991 | Inoue | 600/14 |
| 5,527,259 | 6/1996 | Grace et al. | 600/14 |

FOREIGN PATENT DOCUMENTS

| | | |
|---|---|---|
| 25 78 428A | 9/1986 | France . |
| 2510173 | 9/1976 | Germany . |
| 31 06060 | 9/1992 | Germany . |
| 40 40 96767 | 3/1992 | Japan . |
| 40 41 97272 | 7/1992 | Japan . |
| 20 14 852 C1 | 6/1994 | Russian Federation . |

OTHER PUBLICATIONS

Jacobs, H. Barry, MD; Critical Analysis of Medical Papers Concerning Pulsed electromagnetic Energy (Diapulse).

Niemeyer, Henry J., MD; Wound Healing Stimulation.

Li, Jack and Neurath, Peter W.; Electric and Magnetic Fields Near a Circular Loop at 27 MHz; IEEE Transactions on Bio–Medical Engineering, Jan. 1969.

Wilson, D.H. and Jagadeesh, P.; The Effects of Pulsed Electromagnetic Energy on Peripheral Nerve Regeneration; Annals of the New York Acadmeny of Sciences, vol. 238, pp. 575–580, Oct., 1974.

Raji, A.R.M. and Bowden, R.E.M.; Effects of High–Peak Pulsed Electromagnetic Field on the Degeneration and Regeneration of the Common Peroneal Nerve in Rats; The Journal of Bone and Joint Surgery; vol. 65B, No. 4, Aug., 1983.

Fenn, J.E., MD; Effect of Pulsed Electromagnetic Energy (Diapulse) of Experimental Hematomas; The Canadian Medical Association Journal; vol. 100, pp. 251–254; Feb. 1, 1969.

Nadasdi, Miklos, MD; Inhibition of Experimental Arthritis by Athermic Pulsating Short Waves in Rats; Arthritis.

Goldin, J.H, et al.; The Effects of Daipulse on the Healing of Wounds; a Double–blind Randomised Controlled Trial in Man; British Journal of Plastic Surgery.

Bentall, R.H.C. and Edestein, H.B.; A Trial Involving the Use of Pulsed Electro–magnetic Therapy on Children Undergoing Orchidopexy; Originalarbeiten; vol. 17, No. 4, Nov., 1975.

Barclay, V. et al.; Treatment of Various Hand Injuries by Pulsed Electromagnetic Energy (Diapulse) Physiotherapy, vol. 60, No. 6, pp. 186–189 1983.

Itoh, Masayoshi, MD, et al.; Accelerated Wound Healing of Pressure Ulcers by Pulsed High Peak Power Electromagnetic Energy (Diapulse); Decubitus, Feb., 1991.

Silver, Harold, MD; Reduction of Capsular Contracture with Two–Stage Augmentation Mammaplasty and Pulsed Electromagnetic Energy (Diapulse Therapy); Plastic and Reconstructive Surgery, vol. 69, No. 5, May, 1982.

(List continued on next page.)

*Primary Examiner*—Max Hindenburg
*Assistant Examiner*—Brian Szmal

[57] ABSTRACT

An apparatus and method for toning tissue and particularly skin with a focused, coherent electromagnetic field employ a housing, a user-accessible switch positioned on the housing, and electronics and an electromagnet assembly positioned within the housing. The electromagnet assembly includes a static magnet and an electromagnet which are assembled relative to each other and positioned within the housing such that negative magnetic poles of the static magnet and the electromagnet both face outwardly from an end portion of the housing. The electronics provide a periodic current depending upon a setting of the switch. The electromagnet assembly generates a focused, coherent electromagnetic field in response to the periodic current.

20 Claims, 2 Drawing Sheets

OTHER PUBLICATIONS

Cuocolo, R. et al.; Diapulse Therapy in the Treatment of Vertebral Column Neoplastic Pain; Paper presented at joint meeting of the European Chapters of the International Association for the Study of Pain, May, 1983.

Ionescu, Prof. Agrippa, MD, et al.; Study of Efficiency of Diapulse Therapy on the Dynamics of Enzymes in Burned Wound; Presented at the Sixth International Congress on Burns, Aug. 31, 1982, San Francisco, California.

Rhodes, Lord Cecil, DDS; The Adjunctive Utilization of Diapulse Therapy (Pulsed High Peak Power Electromagnetic Energy) in Accelerating Tissue Healing in Oral Surgery; Datapulse Therapy, vol. 39, No. 4, Jul., 1981 continued in vol. 40, No. 1, Oct., 1981.

Aronofsky, David H., DDS; Reduction of dental postsurgical symptoms using nonthermal pulsed high–peak–power electromagnetic energy; Oral Surgery; vol. 32, No. 5, Nov., 1971.

Erdman II, William James, MD; Peripheral Blood Flow Measurements During application of Pulsed High Frequency currents; General Orthopedics.

Valtonen, Erkki J., et al.; Effects of three modes of application of short wave diathermy on the cutaneous temperature of the legs; Europa Medicophysica.

Hedenius, Per, MD, et al.; Some Preliminary Investigations on the Therapeutic Effect of Pulsed Short Waves in Intermittent Claudication; Current Therapeutic Research, vol. 8, No. 7, Jul., 1966.

Bornstein, Leo A., MD; Acceleration of Transfer of Tube Pedicles and Flaps.

Wilson, David H., FRCS; Tenosynovitis, Tendovaginitis and Trigger Finger; Physiotherapy, vol. 69, No. 10, Oct., 1983.

Fenn, John E., MD; The Therapeutic Value of Pulsed Electromagentic Energy (Diapulse) in the Treatment of the Post Partum Patient; Paper presented at Regional Meeting of the American Academy of Obstetrics and Gynecology, Indianapolis, Indiana, Sep. 22, 1967.

Kaplan, Earl G. and Weinstock, R.E.; Clinical Evaluation of Diapulse as Adjunctive Therapy Following Foot Surgery; Journal Of The American Podiatry Association; vol. 58, No. 5.

Hersh, Bernard J.; The Adjunctive Application of Diapulse Therapy for Foot Traumas; Current Podiatry, Feb., 1972.

Rubik, Beverly; Bioelectromagnetics and the Future of Medicine; Administrative Radiology; Aug., 1997.

Minck, Robert H.; The Ultimate Facial.

Kreguel, Louis, MD; Skin Deep; Dermascope Magazine, Sep./Oct. 1988.

Abstract—Tardy effect of neurogenic muscular atrophy by magnetic stimulation; Am J Phys Med Rehabil 1994 Jul.–Aug.; 73(4):275–9.

Abstract—Skin symptoms after ther eduction of electric fields from visual display units; Scand J Work Environ Healath 1995 Oct.; 21 (5):335–44.

Abstract—Movement of dissolved oxygen in a constant magnetic field; Biofizika 1978 Jan.–Feb.:23(1):159–61.

Abstract—Experimental study using a direct current electrical field to promote peripheral nerve regeneration; J Reconstr Microsurg 1995 May;11(3):189–93.

Abstract—Factors influencing the repair and adaptation of muscles in aged individuals: satellite cells and innervation; J Gerontol A Biol Sci Med Sci 1995 Nov.;50 Spec No():96–100.

Abstract—Depth–target efficient gene delivery and expression in the skin by pulsed electric fields: an approach to gene therapy of skin aging and other diseases; Biochem Biophys Res Commun 1996 Mar. 27; 220(3): 633–6.

Abstract—Measurement of the activating function of magnetic stimulation using combined electrical and magnetic stimuli; J Med Eng Technol 1995 Mar.–Jun.;19(2–3): 57–61.

Abstract—Magnetically induced muscle contraction is caused by motor nerve stimulation and not be direct muscle activation; Muscle Nerve 1994 Oct.;17(10): 1170–5.

Abstract—Patino, O., et al.; Pulsed electromagnetic fields in experimental cutaneous wound healing in rats; Journal of Burn Care & Rehabilitation, 1996 Nov.–Dec.; 17 (6 part 1): 528–31.

Abstract—Isakov, E., et al.; Electromagnetic stimulation of stump wounds in diabetic amputees; Journal of Rehabilitation Sciences 1996; 9(2): 46–8.

Abstract—Markov MS and Pilla AA; Review: electromagnetic field stimulation of soft tissues: pulsed radio frequencey treatment of post–operative pain and edema; Wounds: A Compendium of Clinical Research and Practice; 1995 Jul.–Aug.; 7(4):143–51.

Abstract—Mayrovitz, HN and Larsen, PB; A preliminary study to evaluate the effect of pulsed peri–ulcer skin microcirculation of diabetic patients; Wounds: A compendium of clinical Research and Practice 1995 May–Jun.; 7(3):90–3.

Abstract—McLeod KJ and Rubin CT; Clinical use of electrical stimulation in fracture healing; Physical Medicine and Rehabilitation: State of the Art Reviews, 1995 Feb.; 9 (1):67–76.

Abstract—Stetkarova I, et al.; Characteristics of the silent period after transcranial magnetic stimulation; American Journal of Physical Medicine & Rehabilitation 1994 Apr.; 73 (2) : 98–102.

Abstract—Engebretson J. and Wardell D; A contemporary view of alternative healing modalities; Nurse Practitioner: American Journal of Primary Health Care 193 Sep.; 18(9) : 51–5.

Abstract—Currier, DP, et al.; Effects of electrical and electromagnetic stimulation after anterior cruciate ligament reconstruction; Journal of Orthopaedic and Sports Physical Therapy; 1993 Apr.; 17(4) : 177–84.

Abstract—Martin CJ, et al.; Electromagnetic fields from therapeutic diathermy equipment: a review of hazards and precautions; Physiotherapy; 1991 Jan.; 77(1):3–7.

Abstract—Frank R; Treatment of the perineum by pulsed electro magnetic therapy . . . obstetric and cynacological patients; Midwives Chronical; 1985 Nov.; 98 (1174): 297–8.

Safety Guide for Experiments at CERN 1995 (Excerpt).

Advertisement: M+ Flexible Magnetic Pads; MTT Inc.; Internet Web page at http://www.nutrimed.com/Magnetic.htm.

Advertisement: Bio–Pulse(tm) 3000 Cordless Magnetic Therapy; Internet at http://www.nmia.com/~pegasus/bio3000.html.

Internet Article: Your Health, Jim Townsend's Magnets at http://206.171.105.130:80/magnets/heapow/.

LA Times Article: The Buzz Over Electric Wrinkle Remover; Feb. 2, 1988, Part V.

Article from Internet: How magnetic Fields Affect the Living Body; at http://www.nutrimed.com./Biomag.htm.

Article from Internet: Magnetic Therapy at http://www.lonet.ca/comm/.../history/history.htm.

Advertisement: The Electric Facelift; Allied Health Digest.

Advertising: Various Magnetic products from Internet at http://www.lonet.ca/comm/magna–pak/tens/tens.htm.

Advertising: Exerpt from brochure Anti–Aging International, Inc.

Magnetic Field Therapy; Alternative Therapies; pp. 330–338.

FIG. 1
FIG. 2
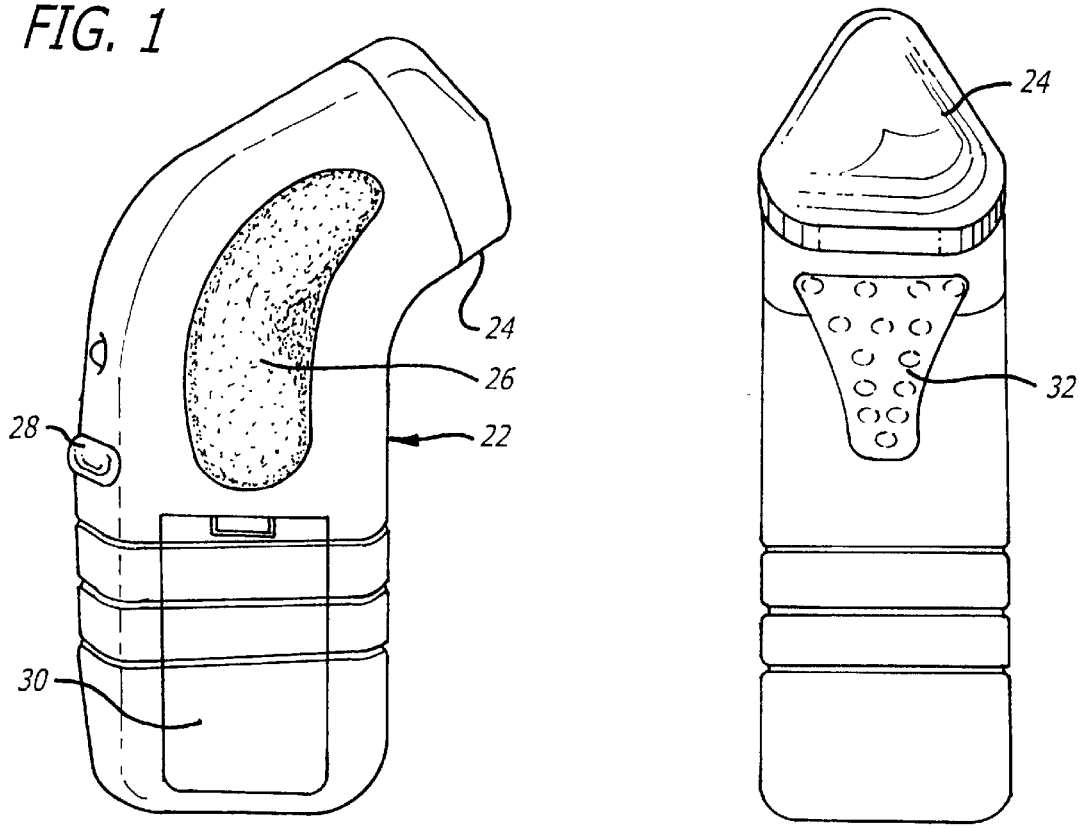
FIG. 3
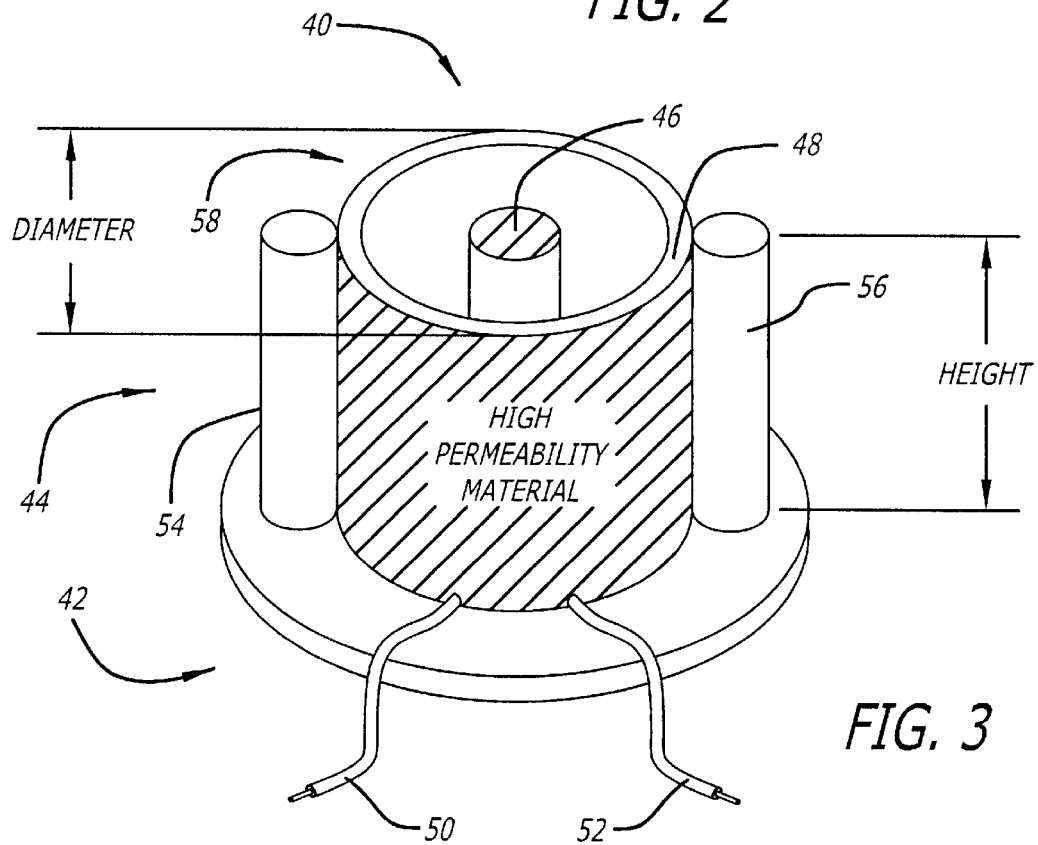

APPARATUS AND METHOD FOR TONING TISSUE WITH A FOCUSED, COHERENT ELECTROMAGNETIC FIELD

BACKGROUND OF THE INVENTION

1. Field of the Invention

The present invention relates to an apparatus and method for toning tissue and, more particularly, pertains to an apparatus and method for toning skin with a focused, coherent electromagnetic field.

2. Description of the Related Art

Since the dawn of the mirror, man has sought ways to conceal, slow, and even reverse the signs of aging. As a result of the aging process, the tone and other characteristics of the skin change. Wrinkles in the skin, sagging and dryness are but a few symptoms and, unfortunately, these imperfections are particularly visible on the face which is almost always exposed.

Prior attempts to eliminate the signs of aging having involved a variety of products and procedures including makeup and face creams, chemical peels, and, more drastically, facial surgery. While makeup and creams may conceal or temporarily soften skin defects and, in some instances, provide nutrients to the skin, they do not address the fundamental problem of a deterioration in the tone of the skin. Chemical peels and facial surgery do nothing to directly address the problem of skin tone deterioration with age. Furthermore, these procedures are expensive, undesirable to many people, and sometimes accompanied with negative side effects. Clearly, there is a need for a safe, affordable and nonevasive method for improving the tone of skin.

Magnets and devices adapted to generate controlled magnetic fields have been used in many different medical applications. For example, magnetic resonance imaging (MRI) is replacing x-ray diagnosis because it is safer and more accurate, and magnetoencephalography is now replacing electoencephalography as the technique of choice for recording electrical activity of the brain. Magnetic field therapy has also been used in the treatment of cancer, rheumatoid disease, infections and inflammations, headaches and migraines, insomnia and sleep disorders, and other ailments. However, there is no known apparatus or method for toning skin with a focused, coherent electromagnetic field.

OBJECTS AND SUMMARY OF THE INVENTION

Thus, it is an object of the present invention to provide an apparatus or method for toning tissue with a focused, coherent electromagnetic field.

In accordance with a specific illustrative embodiment of the present invention, an apparatus for toning tissue with a focused, coherent electromagnetic field includes a housing, a user-accessible switch positioned on the housing, electronics secured within the housing, and an electromagnet assembly. The housing is shaped to be hand-held and includes an end portion. The switch is manipulable into a plurality of switch settings. The electronics are adapted to provide a source of periodic current pulses at one of a plurality of pulse rates depending upon which of the switch settings is selected. The electromagnet assembly is electrically connected to the electronics and fitted within the housing. The electromagnet assembly includes an electromagnet positioned adjacent to the end portion and oriented such that a negative magnetic pole of the electromagnet faces outwardly from the housing. The electromagnet assembly includes a static magnet oriented such that a negative magnetic pole of the static magnet is directed toward the end portion. The electromagnet assembly generates a focused, coherent electromagnetic field in response to the current pulses.

In another aspect of the present invention, an apparatus for toning tissue with a focused, coherent electromagnetic field includes: a housing; electronics secured within the housing and adapted to provide a current; and an electromagnet assembly electrically connected to the electronics and fitted within the housing, the electromagnet assembly including a static magnet and an electromagnet oriented such that negative magnetic poles of the static magnet and the electromagnet face a common direction, the electromagnet assembly generating a focused, coherent electromagnetic field in response to the current.

In another aspect of the present invention, a method for toning tissue with a focused, coherent electromagnetic field includes the steps of: employing an electromagnet assembly to generate a focused, coherent electromagnetic field, the electromagnetic assembly including a static magnet and an electromagnet oriented such that negative magnetic poles of the static magnet and the electromagnet face a common direction; and positioning the electromagnet assembly relative to a surface of a tissue such that a current is induced in the tissue. Furthermore, the positioning of the electromagnet assembly may include moving the electromagnet assembly over an area of the tissue to be treated.

The electromagnet assembly employed in the method for toning tissue is adapted in a further aspect of the present invention to generate one of a plurality of pulsed magnetic fields each with a different pulse rate, and the step of positioning the electromagnet assembly further includes positioning the electromagnet assembly relative to the surface of the tissue for a predetermined length of time depending upon which of the pulsed magnetic fields is being generated by the electromagnet assembly.

DESCRIPTION OF THE DRAWINGS

Other objects, features and advantages of the invention will become readily apparent upon reference to the following detailed description when considered in conjunction with the accompanying drawings, in which like reference numerals designate like parts throughout the figures thereof, and wherein:

FIG. 1 is a front view of an exemplary preferred embodiment of an apparatus for toning tissue with a focused, coherent electromagnetic field according to the present invention;

FIG. 2 is a side view of the apparatus for toning tissue of FIG. 1;

FIG. 3 is a perspective view of an electromagnetic assembly of the apparatus for toning tissue of FIG. 1;

DETAILED DESCRIPTION OF THE PREFERRED EMBODIMENTS

Figure 4:
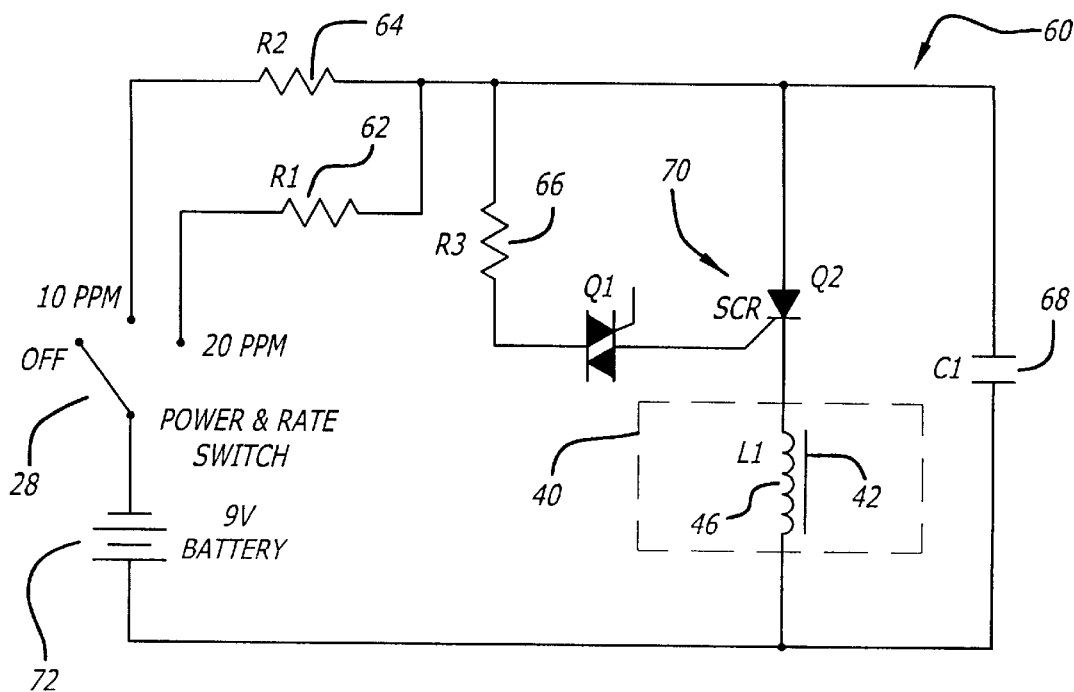
FIG. 4 is an electrical schematic of electronics of the apparatus for toning tissue of FIG. 1.

As shown in FIG. 1, an exemplary, preferred apparatus 20 for toning tissue with a focused, coherent electromagnetic field includes a housing 22 with an end portion 24. An electromagnetic assembly is fitted within the end portion 24. Preferably, the housing 22 and the end portion 24 are formed of a moldable, plastic material.

Generally, the electromagnetic assembly produces a focused, coherent electromagnetic field which, in conjunction with movement of the apparatus 20 across the tissue, e.g., skin, induces a flow of microcurrent through the tissue from the surface. Therefore, the housing 22 is preferably sized and shaped in view of ergonomic considerations such as a desire to provide an apparatus that is comfortable to hold in the hand of a typical intended user. To this end, the illustrated exemplary housing 22 includes an indented portion 26 sized and positioned to receive a finger or fingers of the user to facilitate better gripping of the toning apparatus 20. A sliding, multi-position switch 28 is positioned on the outside of the housing 22 so that it is easily manipulated by the thumb. The switch 28 is electrically connected to electronics within the housing which provide an input current to the electromagnetic assembly as discussed in greater detail with reference to FIGS. 3 and 4. A removable panel 30, e.g., a plastic snap-fit panel, provides access to a battery within the housing 22 that provides power to the electronics.

Referring to FIG. 2, the preferred toning apparatus 20 also includes a pad 32 attached to the housing 22 and positioned as shown. An exemplary pad 32 comprises a rubber pad formed with a textured surface which makes it easier to grip the apparatus 20 particularly when the hands of the user are wet. A preferred housing 22 is waterproof to prevent damage to the electronics positioned therein and any possibility of electrical shock to the user. It should be understood that the scope of the present invention additionally encompasses a toning apparatus 20 that includes an electric shaver mechanism, vibration unit, and/or a heating element in or adjacent to the end portion 24.

FIG. 3 is a perspective view of an electromagnetic assembly 40 of the toning apparatus 20. The electromagnetic assembly 40 is electrically connected to the electronics within the housing 22 and includes a static magnet 42 and an electromagnet 44. The electromagnet 44 is positioned adjacent to the end portion 24 and oriented such that a negative pole of the electromagnet 44 faces outwardly from the housing 22. The static magnet 42 provides a baseline field and is oriented such that a negative pole of the static magnet 42 is also directed toward the end portion 24 of the housing 22. Preferably, the static magnet 42 and the electromagnet 44 are oriented such that their negative poles face a common direction, directed outwardly from the end portion 24 of the housing 22, along a common axis.

An exemplary electromagnet 44 includes a core with a conventional solid center 46 and a surrounding high-permeability material 48 to maximize inductance and reduce size. Inductance is preferably no less than 3.5 Henry. The center 46 has a cylindrically-shaped outer surface about which a coil is wrapped. The high-permeability material 48 is shaped as a cylinder with its inner surface circumferentially positioned relative to the outer surface of the core center 46. The electromagnet 44 also includes electrical leads 50, 52 which are part of the coil. The electronics provide a current to the electromagnet 44 via the electrical leads 50, 52. The current should not exceed 50 mA with peaks of 100 mA. The electromagnet 44 also includes field directors 54, 56 attached at opposing sides of the core as shown. Exemplary field directors 54, 56 are comprised of iron or steel. Preferably, the outside diameter of the high-permeability material 48 is approximately equal to the height of the field directors 54, 56. The static magnet 42 comprises, for example, a toroid permanent magnet or ceramic round or bar magnet which is slightly larger than the outer diameter of the core. The electromagnetic assembly 40 also includes a cover (not shown) secured over the core.

In order to direct the negative poles of the static magnet 42 and the electromagnet 44 outwardly from the end portion 24, the electromagnetic assembly 40 is positioned within the housing 22 adjacent to the end portion 24 and oriented such that an outer surface 58 of the electromagnet 44 faces outwardly from the end portion 24.

A key aspect of the present invention is that the toning apparatus 20 generates a "focused" field. The field generated by the toning apparatus 20 is "focused" because the inductor coil is positioned in front of the static magnet 42. Although this configuration is preferred, it is contemplated that the static magnet 42 could alternatively be positioned in front of the inductor coil.

Another key aspect of the present invention is that the toning apparatus 20 generates a "coherent" field. More specifically, the preferred toning apparatus 20 generates a unipolar, negative polarity only field.

FIG. 4 shows electronics 60 of the toning apparatus 20 which are secured within the housing 22 and adapted to provide a current to the electromagnet assembly 40 via leads 50, 52. The electronics 60 are designed to control the current such that the electromagnetic assembly 40 generates a unipolar, negative polarity only field in response to the current. The unipolar, negative polarity nature of the field is important because it has been observed that microcurrents induced in the tissue have a different effect depending upon the polarity of the inducing field. The amount of flux employed and pulse rate also influence how the tissue reacts to the microcurrents induced therein. At higher pulse rates (above 50 pulses per second), muscle fatigue can result when the nerves in the tissue are pulsed.

A positive pole tends to increase blood flow in tissue, particularly skin. So does a negative pole, but to a lesser extent. However, a negative pole also repels water molecules which are charged negatively and attracts oxygen, hemoglobin, and antioxidants which are charged positively. Since oxygen reduction causes wrinkles, as is evidenced by the fact that the skin of smokers often appears to age faster than non-smokers, a negative pole configuration improves the tone of the skin by counteracting oxygen reduction. Furthermore, the attraction of blood to the skin adds color to the complexion.

When a lower pulse rate (below 50 pulses per second) and a negative pole are used, toning results after a few minutes of use, while avoiding the muscle fatigue caused by higher pulse rates. It has been observed that a slight swelling may result if the apparatus 20 is used for more than approximately 10 minutes even with a lower pulse rate.

Another key aspect of the present invention is that the induced microcurrents stimulate the muscles in the effected area by stimulating the nerves leading to these muscles. In fact, application of the toning apparatus 20 increases muscle tone in the effected area, improves connection of the nerves to these muscles (which often deteriorate with age), and improves nerve conduction. Other observed benefits provided by the present invention include: accelerated turnover of skin cells resulting in younger appearing skin, reduction in pore size, increased oil secretions resulting in reduced skin dryness, increased protein synthesis, and accelerated healing of the skin.

Figure 5:
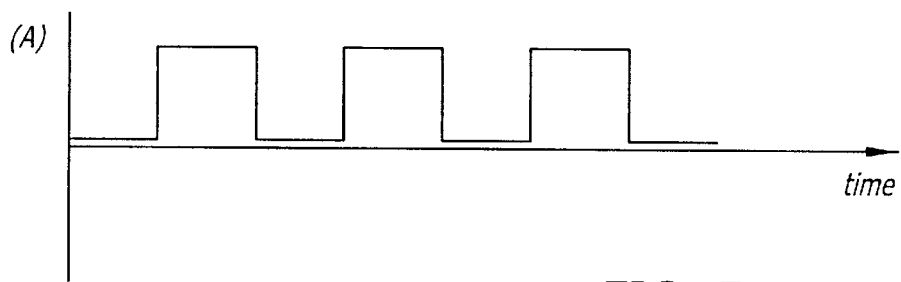
FIG. 5 is a timeline showing a square pulse train provided to the electromagnetic assembly of FIG. 3.
Figure 6:
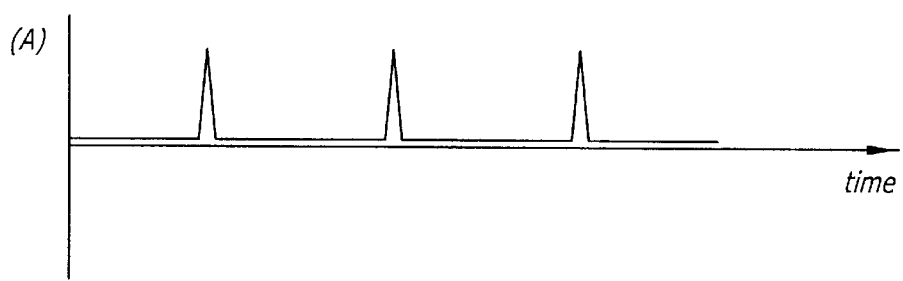
FIG. 6 is a timeline showing a spiked pulse train provided to the electromagnetic assembly of FIG. 3.

Referring again to FIG. 4, the illustrated exemplary electronics 60 include resistors 62, 64, 66, a capacitor 68, a silicon controlled rectifier (SCR) 70, a power source 72, and the power and rate switch 28 configured as shown. The electronics 60 provide a source of periodic current spikes or pulses at one of a plurality of rates depending upon the position of the switch 28. The resistors 62 and 64 are selected depending upon the pulse rates desired for each switch setting. FIGS. 5 and 6 respectively show spiked and square pulse trains of current which are provided by the electronics 60 to the electromagnet assembly 40 depending upon the selection of circuit elements and the particular configuration of the electronics 60. It should be understood that the electronics 60 in FIG. 4 can be modified in a variety of ways such as by providing a pulse generator for generating the square pulse train, providing for pulse width adjustability, etc. Alternating current (AC) can also be provided.

In an exemplary preferred embodiment, the toning apparatus 20 is configured to operate in at least two different modes. An exemplary "immediate toning" mode of operation employs a pulse rate between 6 and 25 pulses per second and can be performed daily for approximately 2 minutes. This mode of operation causes the muscles to contract by stimulating the nerves and repels water which reduces puffiness. A "long-term toning" mode of operation employs a pulse rate of up to 150 pulses per second and, for example, is performed for 10–20 minutes, every 3 days, for 3–6 weeks, and then for 10 minutes, 1 or 2 times per week thereafter. This mode of operation increases blood flow and results in a longer-term toning of the skin.

For both modes of operation, the toning apparatus 20 is moved against the tissue surface covering the entire area to be effected at a rate of movement approximately 1–3 times the rate of movement of a razor during shaving. The static magnet 42, which focuses the field generated by the electromagnet 44, itself induces current in the tissue as a result of its movement throughout the earth's magnetic field. Thus, the static magnet 42 provides a substantially continuous current corresponding to a substantially continuous, e.g., circular, movement of the toning apparatus 20 over the tissue by the user. Preferably, the flux intensity of the field incident upon the area being effected does not exceed 500 milliGauss.

It is also noted that better results may be obtained by increasing skin nourishment (Vitamin A, Vitamin C, Vitamin E, Magnesium, Selenium, grape seed extract) and further increasing skin turnover with alpha hydroxy acids and with retinol, which increases elasticity, or collagen. A liquid toner or salicylic acid can also be used as an adjunct between applications.

Those skilled in the art will appreciate that various adaptations and modifications of the just described preferred embodiment can be configured without departing from the scope and spirit of the invention. For example, the electronics 60 can be modified to provide a "burst mode", e.g., ten bursts in a row with a pulse width of 250 microseconds. Furthermore, it is contemplated that the housing 22 of the toning apparatus 20 can take many forms. For example, the housing 22 can comprise of pair of eyeglasses with two electromagnet assemblies 40 positioned respectively in the arms of the eyeglasses adjacent the skin near the corners of the eyes, a regional mask to cover the face, neck, hands or stomach, or a bed to affect the entire body. Furthermore, the issues effected by the toning apparatus 20 are not limited to skin on the face. For example, the toning apparatus 20 is also suitable for toning muscles of the vagina. Therefore, it is to be understood that, within the scope of the appended claims, the invention may be practiced other than as specifically described herein.

I claim:

1. An apparatus for toning tissue with a focused, coherent electromagnetic field, the apparatus comprising:

a housing shaped to be hand-held and including an end portion;

a user-accessible switch positioned on said housing, said switch being manipulable into a plurality of switch settings;

electronics secured within said housing and adapted to provide a source of periodic current pulses at one of a plurality of pulse rates depending upon which of said switch settings is selected; and an electromagnet assembly electrically connected to said electronics and fitted within said housing, said electromagnet assembly including an electromagnet positioned adjacent to said end portion and oriented such that a negative magnetic pole of said electromagnet faces outwardly from said housing, said electromagnet assembly including a static magnet oriented such that a negative magnetic pole of said static magnet is directed toward said end portion, said electromagnet assembly generating a focused, coherent electromagnetic field in response to the current pulses, the field having an intensity no greater than 500 milliGauss.

2. An apparatus for toning tissue with a focused, coherent electromagnetic field, the apparatus comprising:

a housing;

electronics secured within said housing and adapted to provide a current; and an electromagnet assembly electrically connected to said electronics and fitted within said housing, said electromagnet assembly includes a static magnet and an electromagnet oriented such that negative magnetic poles of said static magnet and said electromagnet face a common direction, said electromagnet assembly generating a focused, coherent electromagnetic field in response to the current, the field having an intensity no greater than 500 milliGauss.

3. The apparatus for toning tissue with a focused, coherent electromagnetic field of claim 2 wherein:

said negative magnetic poles of said static magnet and said electromagnet are aligned along a common axis.

4. The apparatus for toning tissue with a focused, coherent electromagnetic field of claim 2 wherein:

said housing includes an end portion; and said electromagnet is positioned adjacent to said end portion and oriented such that a negative magnetic pole of said electromagnet faces outwardly from said housing.

5. The apparatus for toning tissue with a focused, coherent electromagnetic field of claim 2 wherein:

said housing includes an end portion; and said static magnet is oriented such that a negative magnetic pole of said static magnet is directed toward said end portion.

6. The apparatus for toning tissue with a focused, coherent electromagnetic field of claim 2 wherein the current is a spiked pulse train.

7. The apparatus for toning tissue with a focused, coherent electromagnetic field of claim 2 wherein the current is a square pulse train.

8. The apparatus for toning tissue with a focused, coherent electromagnetic field of claim 2 wherein the current is unipolar.

9. The apparatus for toning tissue with a focused, coherent electromagnetic field of claim 2 wherein the current is periodic.

10. The apparatus for toning tissue with a focused, coherent electromagnetic field of claim 9 wherein:

said electronics are adapted to generate the current at a plurality of pulse rates.

11. The apparatus for toning tissue with a focused, coherent electromagnetic field of claim 9 wherein:

said electronics are adapted to generate the current at a plurality of pulse widths.

12. The apparatus for toning tissue with a focused, coherent electromagnetic field of claim 2 wherein:

said housing comprises an electric shaver housing.

13. A method for toning tissue with a focused, coherent electromagnetic field, the apparatus comprising the steps of:

(a) employing an electromagnet assembly to generate a focused, coherent electromagnetic field having an intensity no greater than 500 milliGauss, said electromagnetic assembly including a static magnet and an electromagnet oriented such that negative magnetic poles of said static magnet and said electromagnet face a common direction; and (b) positioning the electromagnet assembly relative to a surface of a tissue such that a current is induced in the tissue.

14. The method for toning tissue with a focused, coherent electromagnetic field of claim 13 wherein:

said step (b) further comprises moving the electromagnet assembly over an area of the tissue.

15. The method for toning tissue with a focused, coherent electromagnetic field of claim 13 wherein:

the electromagnet assembly is adapted to generate one of a plurality of pulsed magnetic fields each with a different pulse rate; and said step (b) further comprises positioning the electromagnet assembly relative to the surface for a predetermined length of time depending upon which of the pulsed magnetic fields is being generated by the electromagnet assembly.

16. The method for toning tissue with a focused, coherent electromagnetic field of claim 13 wherein:

the electromagnetic field is a pulsed field with a pulse rate selected to stimulate nerves in the tissue.

17. The method for toning tissue with a focused, coherent electromagnetic field of claim 13 wherein:

the electromagnetic field is a pulsed field with a pulse rate less than 50 pulses per second.

18. The method for toning tissue with a focused, coherent electromagnetic field of claim 13 wherein:

the electromagnetic field is a pulsed field with a pulse rate between 6 and 25 pulses per second.

19. The method for toning tissue with a focused, coherent electromagnetic field of claim 13 wherein:

the electromagnetic field is a pulsed field with a pulse rate selected to stimulate a flow of blood in the tissue.

20. The method for toning tissue with a focused, coherent electromagnetic field of claim 13 wherein:

the electromagnetic field is a pulsed field with a pulse rate no greater than 150 pulses per second.

* * * * *